United States Patent [19]

Boudakian

[11] Patent Number: 4,582,935
[45] Date of Patent: Apr. 15, 1986

[54] PROCESS FOR PRODUCING META-AMINOBENZOTRIFLUORIDE

[75] Inventor: Max M. Boudakian, Pittsford, N.Y.
[73] Assignee: Olin Corporation, Cheshire, Conn.
[21] Appl. No.: 685,006
[22] Filed: Dec. 21, 1984
[51] Int. Cl.$^4$ .................. C07C 85/11; C07C 87/60
[52] U.S. Cl. .................... 564/417; 564/442; 570/145
[58] Field of Search ............ 564/417, 442; 570/145

[56] References Cited

U.S. PATENT DOCUMENTS

| | | | |
|---|---|---|---|
| 3,592,861 | 7/1971 | Klauke et al. | 260/646 |
| 3,966,832 | 6/1976 | Lademann et al. | 570/145 |
| 4,005,144 | 1/1977 | Kovar et al. | 564/416 |
| 4,075,252 | 2/1978 | Boudakian | 260/649 |
| 4,145,364 | 3/1979 | Mulvey et al. | 564/417 |
| 4,294,988 | 10/1981 | Tull et al. | 564/417 |
| 4,393,257 | 7/1983 | Nakagawa et al. | 570/145 |
| 4,400,563 | 8/1983 | Ohsaka et al. | 570/144 |
| 4,462,937 | 7/1984 | Ramanadin et al. | 570/145 |

OTHER PUBLICATIONS

B. E. Lawrence et al., "Analytical Chemistry of m-Aminobenzotrifluoride", Manufacturing Chemical and Aerosol News, Jan. 1970, pp. 37–41.

M. M. Boudakian, In M. Grayson and D. Eckroth (Editors), Kirk–Othmer: Encyclopedia of Chemical Technology, vol. 10, 3rd Edition, J. Wiley, N.Y. 1980, "Fluorinated Aromatic Compounds", p. 901.

A. E. Porai-Koshits, et al., *J. Applied Chem. (USSR)*, 28, 921 (1955).

M. Kawamura et al., CA, 82, 3947, (1975).

*Primary Examiner*—Charles F. Warren
*Assistant Examiner*—R. A. Picard
*Attorney, Agent, or Firm*—William A. Simons; Thomas P. O'Day

[57] ABSTRACT

Disclosing a process for making meta-aminobenzotrifluoride comprising:

reacting meta-nitrobenzotrichloride with hydrogen fluoride in the presence of ammonium ions under a pressure of at least about 35 psig and at a temperature of at least about 55° C. for sufficient time in the presence of water and a metal catalyst to form meta-aminobenzotrifluoride, wherein the amount of water added is at least one mole percent of the meta-nitrobenzotrichloride.

6 Claims, No Drawings

PROCESS FOR PRODUCING META-AMINOBENZOTRIFLUORIDE

BACKGROUND OF THE INVENTION

1. Field of the Invention

This invention relates to a process for producing meta-aminobenzotrifluoride.

2. Description of Prior Art

Meta-aminobenzotrifluoride (also known as 3-trifluoromethylaniline or MABTF) is a chemical intermediate to dyes, germicides, pharmaceuticals and crop protection chemicals.

The standard manufacturing route for making MABTF involves the steps of (1) nitration of trifluoromethylbenzene with a nitration agent to form meta-nitrobenzotrifluoride followed by (2) reduction of this intermediate to MABTF by catalytic hydrogenation. See M. M. Boudakian "Fluorinated Aromatic Compounds" *Kirk-Othmer Encyclopedia of Chemical Technology,* Vol. 10, 3rd Edition, pp. 919 and 923. The reduction step may also be carried out using iron filings, HCl and $H_2$ to give MABTF in 74–85% yield. See A. E. Porai-Koshits et al., *J. Applied Chem. (USSR),* 28, p. 921 (1955). However, during the nitration step, the corresponding ortho and para-isomers are also made. See *Manufacturing Chemist & Aerosol News,* January 1970 pp. 37–41. Separation of these unwanted isomers before or after the reduction step is costly and lowers the overall yield of MABTF based on the original starting materials. Furthermore, this route involves multiple handling steps which also raise the cost of the process.

Separately, U.S. Pat. No. 4,393,257 (Nakagawa et al.) teaches that m-nitrobenzotrichloride may be fluorinated with anhydrous HF in a gaseous phase at elevated temperatures and in the presence of $Cl_2$ to obtain primarily meta-nitrobenzotrifluoride. This reference does not suggest that a simultaneous reduction reaction may also occur to form MABTF.

One objective of the present invention is to provide a process for making meta-aminobenzotrifluoride in high purity.

Another objective of the present invention is to provide a process for the simultaneous fluorination-reduction of meta-nitrobenzotrichloride to meta-aminobenzotrifluoride.

Still another objective of the present invention is to provide a process for the high-yield single reactor fluorination-reduction reaction of meta-nitrobenzotrichloride to meta-aminobenzotrifluoride.

BRIEF SUMMARY OF THE INVENTION

The present invention, therefore, is directed to a process for producing meta-aminobenzotrifluoride comprising:

reacting meta-nitrobenzotrichloride with hydrogen fluoride in the presence of ammonium ions under a pressure of at least about 35 psig and a temperature at least about 55° C. for sufficient time and in the presence of water and metal catalyst to form meta-aminobenzotrifluoride, wherein the amount of water added is at least about one mole percent of the meta-nitrobenzotrichloride.

DETAILED DESCRIPTION

The present invention is illustrated by the following equation (A):

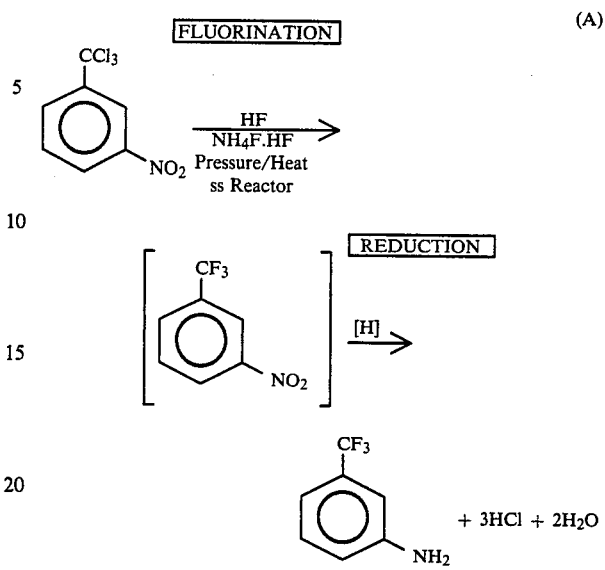

One major improvement of the present invention over that of the prior art is the introduction of $NH_4^+$ in the solution of HF.

The substrate for this reaction, meta-nitrobenzotrichloride, is a commercially available material.

Hydrogen fluoride acts as the source of fluorine for the reaction. Suitably, from about 2 moles up to about 50 moles of HF, preferably about 7.5 moles up to about 40 moles of HF, are employed per mole of substrate. Anhydrous HF is preferred but 70% aqueous up to anhydrous may be employed if desired. The HF should be present in excess molar quantities over that necessary for the fluorination reaction because having too little of HF present will cause the overall reaction to run out of control and endanger the safety of the operation. On the other hand, having too much HF present lowers the economic value of the process. Anhydrous HF is favored because excessive water present may cause corrosion to the reaction equipment if not carefully controlled and may lead to the conversion of the trifluoromethyl group to a carboxyl moiety.

In accordance with the present invention, a solution of hydrogen fluoride containing ammonium ions is utilized as a proton ($H^+$) source for the reduction and to facilitate the fluorination source for both parts of reaction (A). As used herein the term "ammonium ions" is used in a general sense to indicate those ions formed by adding ammonium ion-generating compounds to the solution of hydrogen fluoride. Such compounds can be either ammonium salts such as ammonium fluoride, ammonium bifluoride, ammonium fluoride solvates like $NH_4F.HF$, $NH_4.3HF$, and $NH_4F.5HF$, aqueous or anhydrous ammonia or combinations thereof. Further sources of "ammonium ions" can be other soluble nonfluoride ammonium salts as described in detail below. The preferred source of ammonium ions is ammonium bifluoride because of its relatively low cost and ease of handling.

The structure of the compound or compounds formed when a source of ammonium ions are added to the HF medium has not been ascertained. It is believed that possibly an ammonium fluoride-HF complex is formed which is at least in part, one or more of the above solvates of ammonium fluoride and HF. The generalized formula for these solvates is $NH_4F \cdot xHF$, with x having one or more values in the range of about 1 to 10. It is known, for example, that when ammonium fluoride is added to HF, one or more stable solvates are formed, namely $NH_4F3HF$ having a melting point of $-23°$ C. and/or $NH_4F \cdot 5HF$ having a melting point of $-8°$ C. Also, it is known that when aqueous or anhydrous ammonia is added to HF, there is an instantaneous reaction to form ammonium fluoride. And quite possibly, these solvates are also produced. Likewise, when other ammonium salts like ammonium bifluoride and the like are used, it is also possible that the higher solvates are made. However, this is merely a theory and the present invention is not limited thereto. The important criterion is that some source of ammonium ions be added to the solution of HF in carrying out the present process.

The amount of ammonium ion is most conveniently expressed as a molar percent of the solution of hydrogen fluoride and this molar percent may range from about 0.5 to about 35 percent of the HF solution, preferably from about 2.5 to about 15 molar percent of the HF solution. In figuring this molar percent, only the moles of ammonium ions and those of HF are used; others such as anions of ammonium salts and the like are not used. For purposes of determining these percentages, where ammonium bifluoride is utilized for example, the bifluoride is regarded as contributing one mole of HF and one mole of ammonium ion per mole of the bifluoride.

As stated before, the ammonium ions can be alternatively formed by addition of non-fluoride ammonium salts instead of the addition of the above ammonium compounds to the HF. This is accomplished by adding any suitable soluble non-fluoride ammonium salt or salts to the HF so that the ammonium cation will react with hydrogen fluoride and may form said solvates. These salts should be soluble in the reaction medium so that the ammonium cation remains in solution. The following commercial ammonium salts are illustrative of those which may be employed:

Ammonium Acetate
Ammonium Bicarbonate
Ammonium Pentaborate
Ammonium Bichromate
Ammonium Bromide
Ammonium Chloride
Ammonium Citrate
Ammonium Fluoborate
Ammonium Molybdate
Ammonium Gluconate
Ammonium Lauryl Sulfate
Ammonium Nitrate
Ammonium Oxalate
Ammonium Persulfate
Ammonium Phosphate
Ammonium Silicofluoride
Ammonium Sulfamate
Ammonium Sulfate
Ammonium Thiosulfate
Ammonium Thiocyanate A basis and understanding of this embodiment of the invention wherein a non-fluoride ammonium salt in HF is used can be found in the treatise "Inorganic Chemistry in Liquid HF" by M. F. A. Dove and A. F. Clifford, Pergamon Press, New York, 1971, which states on page 156 that the halides of alkali metals, ammonium and substituted ammonium cations will be solvolyzed very readily to give solution of their fluoride. On the basis of this teaching, soluble non-fluoride ammonium salts can be used to generate ammonium ions in the present invention provided they do not cause any appreciable hindrance or interference of the simultaneous fluorination or reduction reactions. And thus, it is to be understood that the ammonium compounds added to the HF solution may be in the form of either the above-noted ammonium fluoride compounds, ammonia (aqueous or anhydrous), or soluble non-fluoride ammonium salts.

The initial role of water is to serve as an auto-catalyst in the reduction phase of the process. Water subsequently formed from the reduction step can then be recycled for completion of the reduction sequence. The amount of water originally present should be enough to catalyze this reduction step. It is believed amounts of water of at least about 1 mole percent of the meta-nitrobenzotrichloride are needed to be added to catalyze this reaction. It should also be noted that excessive amounts of water are not preferred because of corrosion problems and by-product formation. Preferably, amounts of water over about 30 mole percent of meta-nitrobenzotrichloride are not desirable. Mole ratios of meta-nitrobenzotrichloride to water in the range from about 40:1 to about 5:1 are more preferred.

Any metal catalyst conventionally known to catalyze a hydrogenation reaction of the present type may be employed. Suitable metal catalysts may include iron, tin and zinc. Salts of these metals and impure forms (e.g. steel alloys) may be employed instead. The amounts of these metals to be employed should be sufficient to catalyze the reduction reaction. Preferred amounts of these metals would range from about 5 mole percent to about 25 mole percent of the meta-nitrobenzotrichloride.

The unexpected formation of MABTF instead of the m-nitro intermediate shown in Reaction A is believed to be due to the generation of $H_2$ from $H_2O$, Fe (from the steel reactor wall) and either HCl from the non-vented portion of the by-product HCl or from the ammonium ions present.

It has been found that temperatures higher than about 55° C. with or a sufficiently long reaction time are required for the complete side-chain fluorination of the $-CCl_3$ group to $-CF_3$. Generally, reaction temperatures from about 100° C. to about 150° C. are preferred. The reaction time is largely dependent upon the reaction temperature. Reaction times from about 8 to 100 hours are preferred.

This invention also requires the employment of pressures of at least about 35 psig. Pressures below this level exhibit poor fluorination exchange. Pressures above about 200 psig are not preferred because of the hazards involved and the need of special high pressure equipment. It is preferred to employ pressures in the range from about 65 psig to about 150 psig.

Preferably and advantageously, the metanitrobenzotrichloride is first added to the reactor. Addition of an inert solvent such as methylene chloride is optional. The source of the ammonium ions and the HF is then added and the reactor is heated under pressure to the above-noted temperatures and pressures for a sufficent amount of time until substantially all of the meta-nitrobenzotrichloride is converted to the desired product. The reaction mixture may then be neutralized with a base such as NaOH or ammonium hydroxide and the desired product is recovered from the liquid reaction mixture. This recovery may be accomplished by distillation or other conventional techniques.

The present process can be carried out in any conventional chemical reactor which is suitable for this purpose. While the reactor can be made from stainless steel, water generated from in-situ reduction can cause corrosion. Alternatively, plastic reactors fabricated from polyethylene, polypropylene, polychlorotrifluoroethylene, polytetrafluoroethylene or the related TEFLON PFA Fluorocarbon Resins (featuring perfluoroalkoxy side chains) to which iron powder is added would be suitable vessels to effect in-situ fluorination-reduction.

The present invention also contemplates the employment of other substrates which have the meta-nitrobenzotrichloride structure (i.e. having other constituents on the aromatic ring). For example, such compounds may include 1-nitro-3,5-bis(trichloromethyl)benzene, 2-chloro-5-nitrobenzotrichloride, 2-fluoro-5-nitrobenzotrichloride, 2,4-dichloro-5-nitrobenzotrichloride, 2,4-difluoro-5-nitrobenzotrichloride, 2-chloro-4-fluoro-5-nitrobenzotrichloride, 4-chloro-3-nitrobenzotrichloride, 4-fluoro-3-nitrobenzotrichloride.

The following experiments further illustrate the invention. All parts and percentages are by weight unless explicitly stated otherwise.

EXAMPLE 1

Fluorination-Reduction in Presence of Inert Solvent

The following were charged ($N_2$ atmosphere) into a one liter stainless steel Parr autoclave: m-nitrobenzotrichloride (0.14 moles; 33.5 g. Assay: 94.6%), ammonium bifluoride (0.7 moles; 40.0 g.; 0.6 wt. % $H_2O$, 0.013 mole), methylene chloride (150 ml) and hydrogen fluoride (5.25 moles; 105 ml).

The reactants were then heated in three stages. By-product HCl (plus some HF) was vented into a caustic scrubber.

| STAGE | TEMPERATURE (°C.) | PRESSURE (psig) | TIME (hrs) |
|---|---|---|---|
| (I) | 68–95 | 90–160 | 2.5 |
| (II) | 68–101 | 90–180 | 6.5 |
| (Recharged with additional HF: 5.25 moles (105 ml) | | | |
| (III) | 103–117 | 190–220 | 6.5 |
| | | | 15.5 Hrs |

Assay of the vent gas disclosed 0.232 mole HCl had been evolved.

The 2-phase reaction mixture was neutralized with 15% aqueous ammonia solution and the contents steam-distilled. The steam-distillate was concentrated (50° C./~5 mm) to give a liquid, wt. 16.0 g., $n_D^{23}=1.4778$. (Literature value for m-aminobenzotrifluoride: $n_D^{20}=1.4788$). GC assay (SF-96 column; 120° C.; retention time, 7.04 min.): 99.6%. Correcting for 94.6% assay of m-nitrobenzotrichloride charged, 75.0% in-hand yield of m-aminobenzotrifluoride was obtained.

EXAMPLE 2

Fluorination-Reduction in Absence of Inert Solvent

The following were charged into a 1 liter stainless steel Parr autoclave: m-nitrobenzotrichloride (0.20 mole; 48.09 g., 100% Assay), ammonium bifluoride (1.0 mole; 57.1 g.; 0.6 wt. % $H_2$; 0.019 mole) and hydrogen fluoride (7.5 moles; 150 g.).

The reactants were heated at three stages and HCl vented at stage to determine degree of exchange-fluorination.

| STAGE | TEMPERATURE (°C) | PRESSURE (psig) | TIME (hrs) | HCl EVOLUTION (moles) |
|---|---|---|---|---|
| (I) | 46–75 | 40–150 | 3.0 | 0.306 |
| (II) | 79–96 | 50–105 | 7.0 | 0.122 |
| (III) | 101–127 | 60–120 | 4.0 | none |

The fluorination mixture was neutralized with a 15% aqueous ammonia solution and the product was then extracted with methylene chloride. The lower (organic) layer was phased and concentrated to give a liquid, wt. 20.1 g. (0.125 mole), $n_D^{25}$ 1.4798, which assayed 98.5% m-aminobenzotrifluoride by GC (SF-96 column; 120° C., retention time, 7.17 min.). Product was confirmed by mass spectroscopy and NMR assay. A 62.5% in-hand yield of m-aminobenzotrifluoride was obtained.

COMPARISON 1

HF Alone at Room Temperature and Atmospheric Pressure m-Nitrobenzotrichloride (0.20 mole; 48.09 g., Assay=100%) was added to hydrogen fluoride (65 moles; 100 g.) in a 2-liter stainless steel reactor and the mixture agitated at reflux (max. pot temp., +18° C.) for a 4-hour period. No exchange-fluorination occurred as evidenced by absence of HCl gas evolution.

COMPARISON 2

HF/Ammonium Bifluoride at Moderate Temperatures and Atmospheric Pressure

Ammonium bifluoride (1.0 mole; 57.1 g.; 0.17 wt. % $H_2O$ or 0.0053 mole) and hydrogen fluoride (2.5 moles; 50 g.) were added and the mixture heated from 27°–46° C. over a 4.5-hour period. The reaction mixture was neutralized with a 5% aqueous ammonia solution and then extracted with methylene chloride. The lower organic layer was phased and concentrated to give a liquid, wt. 33.0 g., $n_D^{24}$ 1.5105. Infrared spectral assay gave no evidence for $CF_3$-bands at 1312 cm$^{-1}$ (symmetrical frequency) or at 1172 and 1143 cm$^{-1}$ (antisymmetrical frequencies). GC assay (SF-96 column: 120° C. to 250° C. at 8°/min.) showed two main components which were identified as m-$CF_2ClC_6H_4NO_2$ and m-$CFCl_2C_6H_4NO_2$ by mass spectroscopy:

| STRUCTURE | ASSAY Retention Time (min.) | Area % | IN-HAND YIELD |
|---|---|---|---|
| m-$CF_2ClC_6H_4NO_2$ | 10.28 | 36.38 | 29% |
| m-$CFCl_2C_6H_4NO_2$ | 13.70 | 61.34 | 45% |

COMPARISON 3

HF/Ammonium Bifluoride at Moderate Temperatures and High Pressures

The following were charged into a 1 liter stainless steel Parr autoclave: m-nitrobenzotrichloride (0.14 mole; 33.58 g. Assay 100%), ammonium bifluoride (0.07 mole; 40.0 g.; 0.6 wt. % $H_2O$ or 0.013 moles), methylene chloride (150 ml) and hydrogen fluoride (5.25 moles; 105 ml).

The reactants were heated at 80°–85° C. (7 hours); maximum pressure (135 psig). The 2-phase reaction mixture was neutralized with 15% aqueous ammonia and the contents steam distilled. The steam distillate was concentrated (50° C./~5 mm) to give a liquid, wt. 24.2 g. (83.5% in-hand yield), $n_D^{19}=1.5111$. Literature value for 3-(chlorodifluoromethyl)nitrobenzene, $n_D^{21}$ 1.5043). GC assay (SF-96 column: 120° to 250° C. 8°/min) and mass spectroscopy provided the following product identification:

| STRUCTURE | GC ASSAY | |
|---|---|---|
| | Retention Time (min.) | Area % |
| m-$CF_3C_6H_4NO_2$ | 6.79 | 4.0 |
| m-$CF_2ClC_6H_4NO_2$ | 10.44 | 90.64 |
| m-$CFCl_2C_6H_4NO_2$ | 13.43 | 3.8 |

It is believed that traces of MABTF would be formed if this reaction was carried out for more time such as shown in Example 1 and 2.

COMPARISON 4

Attempted Fluorination of Orthonitrobenzotrichloride

A. Atmospheric Pressure Conditions

1. Absence of Ammonium Bifluoride o-Nitrobenzotrichloride (0.20 mole; 48.09 g.) was added to hydrogen fluoride (5 moles; 100 g.) in a 2-liter stainless steel reactor and the mixture agitated at reflux (max. pot temp., +14° C.) for a 2-hour period. No exchange-fluorination occurred as evidenced by absence of gas evolution (corroborated by scrubber assay for chloride ion).

2. Pressure of Ammonium Bifluoride

Ammonium bifluoride (1.0 mole; 57.1 g.; 0.17% $H_2O$ corresponding to 0.0053 mole) and additional hydrogen fluoride (1 mole; 20 g.) were added and the mixture heated from 25°–51° C. over a 3-hour period. Assay of the caustic scrubber showed negligible HCl evolution (0.032 mole) indicative of insignificant fluorination.

B. Pressure Fluorination: Ammonium Bifluoride Catalyst

The following were charged into a 1 liter stainless steel Parr autoclave: m-nitrobenzotrichloride (0.20 mole; 48.1 g.), hydrogen fluoride (7 moles; 140 g.), ammonium bifluoride (1.0 mole; 57.1 g.; $H_2O$ content, 0.17 wt. % corresponding to 0.0053 mole) and methylene chloride.

The reactants were heated from 52° to 130° C. over a 4-hour period. The reactor was periodically vented to remove HCl (maximum pressure, 170 psig). Assay of the caustic scrubber solution indicated negligible exchange-fluorination (0.024 mole HCl).

The fluorination mixture was neutralized with 15% aqueous ammonia in the presence of additional $CH_2Cl_2$ (300 ml). A significant amount of methylene chloride-$H_2O$ insolubles were noted. These carbonaceous solids were filtered and dried (26.0 g.; corresponding to 54.1% of starting material). Concentration of the methylene chloride extract gave primarily tars. This Part B shows that carrying on the reaction conditions of the present invention with the ortho-nitrobenzotrichloride resulted in product degradation rather than the desired formation of OABTF.

What is claimed is:

1. A process for making meta-aminobenzotrifluoride comprising:
   reacting meta-nitrobenzotrichloride with hydrogen fluoride in the presence of ammonium ions under a pressure of at least about 35 psig and at a temperature of at least about 55° C. for in the presence of water and a metal catalyst to form meta-aminobenzotrifluoride, wherein the amount of water added is at least one mole percent of the meta-nitrobenzotrichloride.

2. The process of claim 1 wherein the source of said ammonium ions is ammonium bifluoride.

3. The process of claim 1 wherein the reaction pressure is from about 65 psig to about 150 psig.

4. The process of claim 1 wherein the reaction temperature is from about 100° C. to about 150° C.

5. The process of claim 1 wherein the amount of water added is from about 1 to about 30 mole percent of said meta-nitrobenzotrichloride.

6. The process of claim 1 wherein said metal catalyst is iron.

* * * * *

UNITED STATES PATENT AND TRADEMARK OFFICE
CERTIFICATE OF CORRECTION

PATENT NO. : 4,582,935

DATED : April 15, 1986

INVENTOR(S) : Max M. Boudakian

It is certified that error appears in the above-identified patent and that said Letters Patent is hereby corrected as shown below:

In column 4, at line 58 delete "metanitrobenzo-" and insert --meta-nitrobenzo---.

In column 5, at line 67 delete "$H_2$;" and insert --$H_2O$;--.

In column 6, at line 28 delete "(65 moles;" and insert --(5 moles;--.

In column 8, at line 5 delete "m-nitrobenzotrichloride" and insert --o-nitrobenzotrichloride--.

In column 8, at line 33 after "for" and before "in" insert --sufficient time--.

Signed and Sealed this

Twenty-ninth Day of July 1986

[SEAL]

Attest:

DONALD J. QUIGG

Attesting Officer     Commissioner of Patents and Trademarks